United States Patent
Joines

(10) Patent No.: US 7,601,936 B2
(45) Date of Patent: Oct. 13, 2009

(54) MICROWAVE SYSTEM AND METHOD FOR CONTROLING THE STERLIZATION AND INFESTATION OF CROP SOILS

(76) Inventor: William Thomas Joines, 4010 Deepwood Cir., Durham, NC (US) 27707

( * ) Notice: Subject to any disclaimer, the term of this patent is extended or adjusted under 35 U.S.C. 154(b) by 155 days.

(21) Appl. No.: 11/329,629

(22) Filed: Jan. 11, 2006

(65) Prior Publication Data

US 2006/0186115 A1    Aug. 24, 2006

Related U.S. Application Data

(60) Provisional application No. 60/643,015, filed on Jan. 11, 2005.

(51) Int. Cl.
  *H05B 6/64* (2006.01)
  *A01C 15/00* (2006.01)
(52) U.S. Cl. .................. 219/695; 219/678; 111/118
(58) Field of Classification Search ............. 219/695, 219/678, 679, 738, 748, 690; 404/77, 79, 404/91, 95, 108, 111; 89/1.11, 1.13; 111/118, 111/200; 405/128.85
See application file for complete search history.

(56) References Cited

U.S. PATENT DOCUMENTS

| | | | | |
|---|---|---|---|---|
| 4,319,856 | A | * | 3/1982 | Jeppson ................. 404/79 |
| 5,141,059 | A | | 8/1992 | Marsh |
| 5,287,818 | A | | 2/1994 | Rajamannan |
| 6,401,637 | B1 | * | 6/2002 | Haller .................. 111/118 |
| 6,485,690 | B1 | | 11/2002 | Pfost et al. |
| 6,647,661 | B2 | | 11/2003 | Grigorov |
| 6,943,034 | B1 | | 9/2005 | Winkler et al. |
| 2003/0070677 | A1 | | 4/2003 | Handique et al. |
| 2005/0045238 | A1 | | 3/2005 | Yang et al. |
| 2005/0166980 | A1 | | 8/2005 | Unger et al. |
| 2006/0078383 | A1 | * | 4/2006 | Novak ................... 404/79 |

FOREIGN PATENT DOCUMENTS

| | | |
|---|---|---|
| EP | 1 525 916 A1 | 4/2005 |
| WO | WO 01/04909 A1 | 1/2001 |

OTHER PUBLICATIONS

International Search Report and Written Opinion from PCT/US2006/000890 dated Jun. 7, 2006.

W.T. Joines, "Frequency Dependent Absorption of Electromagnetic Energy in Biological Tissue", IEEE Transactions on Biomedical Engineering, vol. BME-31, pp. 17-20, Jan. 1984 (article in journal).

(Continued)

*Primary Examiner*—Quang T Van
(74) *Attorney, Agent, or Firm*—Moore & Van Allen, PLLC; R. Brian Drozd

(57) ABSTRACT

The method and the system are applicable in farming activities, pest control, industry, agriculture, forestry, etc. for controlling insects and other plant pests from crops. The system performing the method comprises a source of lethal impact which is a microwave generator with a microwave guiding element directed so as to infested soil. The microwave energy is transferred from a microwave generator into the pests located in the desired soil location, killing the plant insects and pests.

14 Claims, 5 Drawing Sheets

OTHER PUBLICATIONS

P. Debye, "Polar Molecules", New York: Chemical Catalog, 1929 (book).

W.T. Joines, "Frequency Dependent Absorption of Electromagnetic Energy in Biological Tissue", IEEE Transactions on Biomedical Engineering, vol. BME-31, pp. 17-20, Jan. 1984 (article in journal).

P. Debye, "Polar Molecules", New York: Chemical Catalog, 1929 (book).

* cited by examiner

MICROWAVE SYSTEM AND METHOD FOR CONTROLING THE STERLIZATION AND INFESTATION OF CROP SOILS

PRIORITY

The present application claims priority from provisional patent application 60/643,015 filed on Jan. 11, 2005, which is herein incorporated by reference.

BACKGROUND OF THE INVENTION

1. Field of Invention

The present invention relates generally to microwave antennas, sources and leakage protection mechanisms, and more specifically to a directed-energy microwave system for irradiating crop soils to control infestation.

2. Brief Description of the Related Art

By way of background to the ensuing discussion of the related art to the present invention, and in connection with the description of the invention hereinafter, set out below is a glossary of relevant terminology.

As used herein, "soil" includes the soil and living organisms in the ground that are harmful to plants (e.g. insects).

As used herein, "microwave" means a microwave generator or microwave energy source.

As used herein, "insects" refer to any living organism which may be harmful to plants. The definition, as used herein, is not limited to the typical meaning of an insect, but to other creatures, such as worms, bacteria, and other creatures of harm to plants or that feed off of plants.

As used herein, "vehicle" refers to any apparatus that may be operated or placed in motion.

The world's food supply is being greatly diminished because of infestation of fruit and vegetable plants by insects that attack the root system within the soil. The problem is partially controlled by the fumigation of chemical pesticides into the soil after harvest and before planting. However, a potentially more serious problem is created by the accumulation of chemical pesticides in the soil. The pesticides will eventually filter down to the water table, and run-off will occur during rains or irrigation. This diminishes the purity of the water we use for drinking, cooking and bathing. Also, workers applying the pesticides are subjected to a degree of risk to their short-term and long-term health.

Therefore, there is a continuing and unaddressed need in the art for sterilization for crop soil without the use of harmful pesticides.

SUMMARY OF THE INVENTION

The present invention relates to a microwave source system for controlling the sterilization of infestation of crop soil.

The present invention replaces the chemical pesticide system with a directed energy system that leaves no residual pollutants in the soil after the energy source is switched off.

The present invention uses a portable microwave generator that is connected to an applicator that transfers microwave energy from the portable generator into the soil along the rows that will be used for planting. Both the generator and applicator are mounted on a vehicle that moves over the tops of the rows at a predetermined speed. A lethal amount of microwave energy is transferred into the soil to be absorbed within the insects in the soil. An integral part of this directed energy system is leakage suppressors that keep the microwave energy directed into the soil and not into the surrounding environment.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE INVENTION, AND PREFERRED EMBODIMENTS THEREOF

The present invention relates to a microwave apparatus designed to control the infestation of harmful insects, worms, bacteria and anything else harmful to crops or plants.

Figure 1:
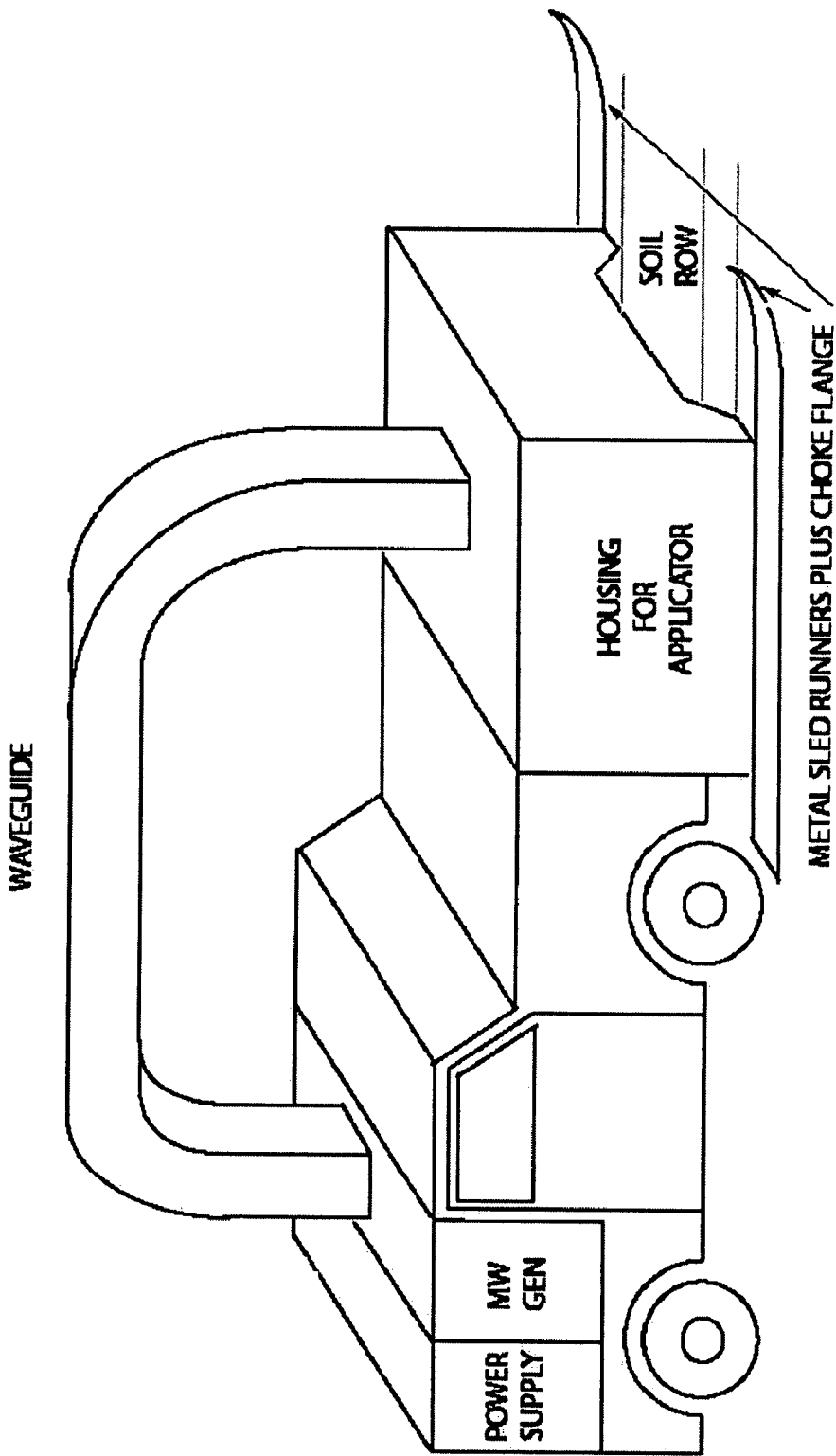
FIG. 1 shows an application of the present invention where the microwave system is attached to a vehicle.
Figure 2:
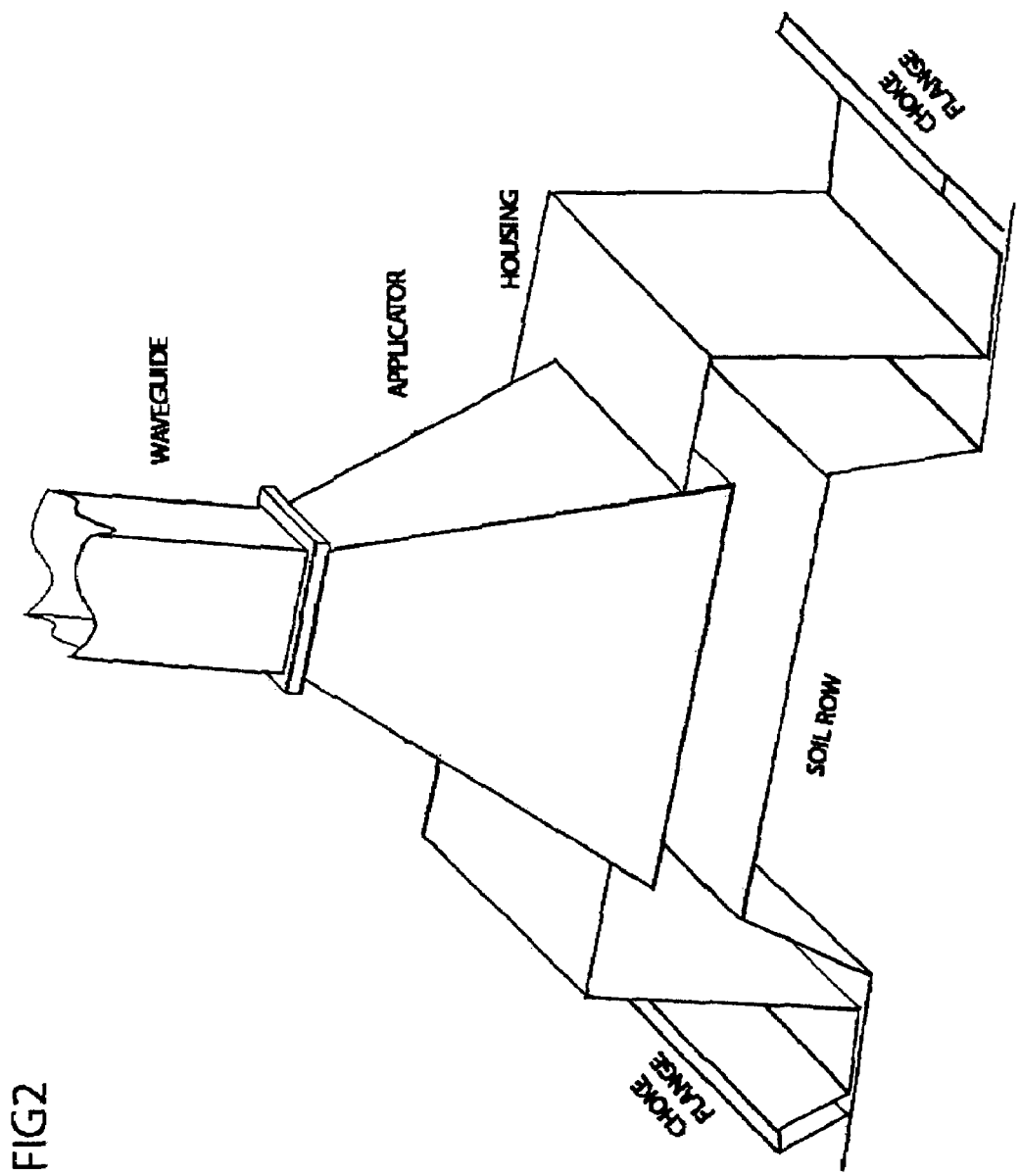
FIG. 2 is a three dimensional view of the present invention.
Figure 3:
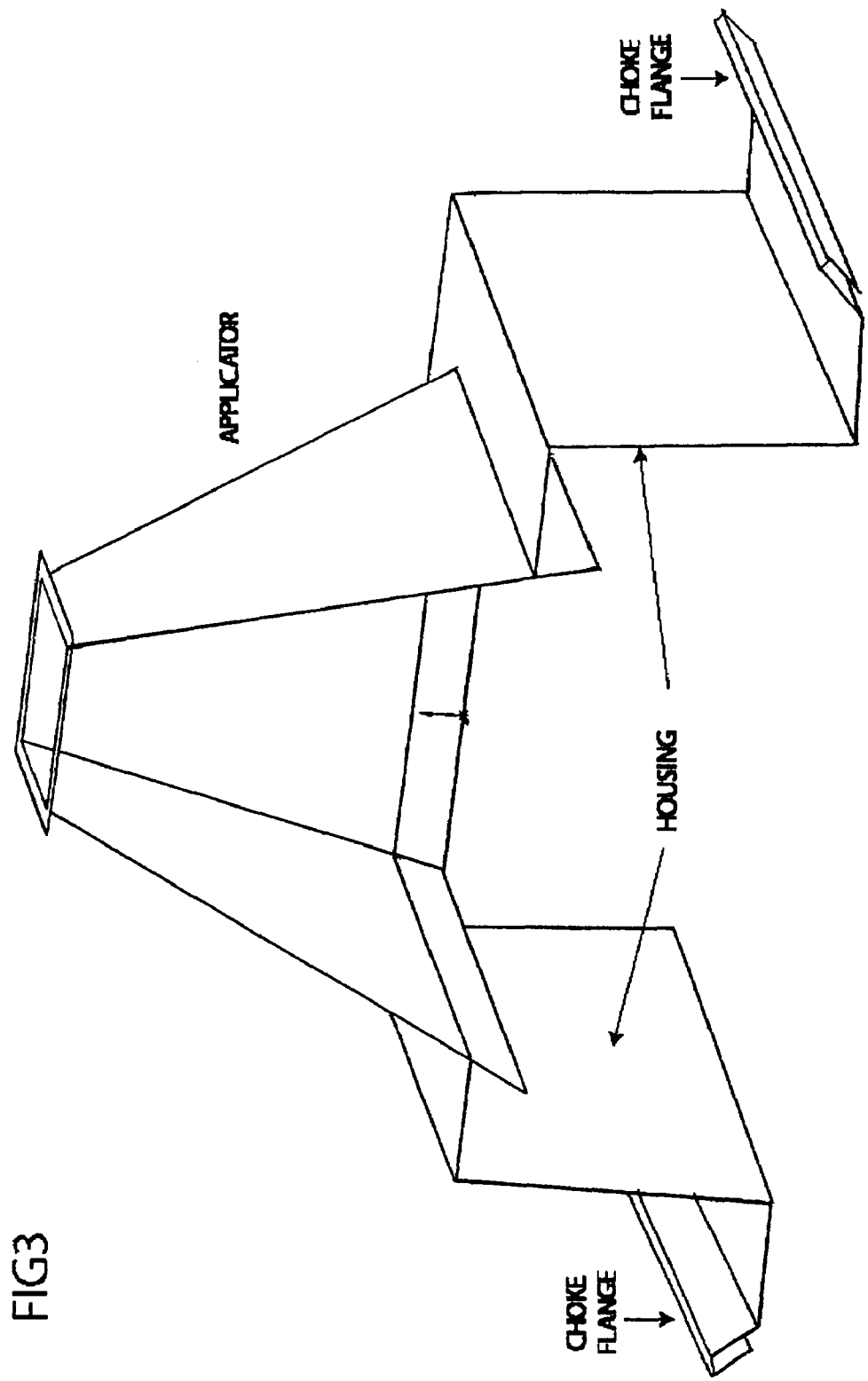
FIG. 3 is a three dimensional view of a cross section of the present invention.
Figure 4:
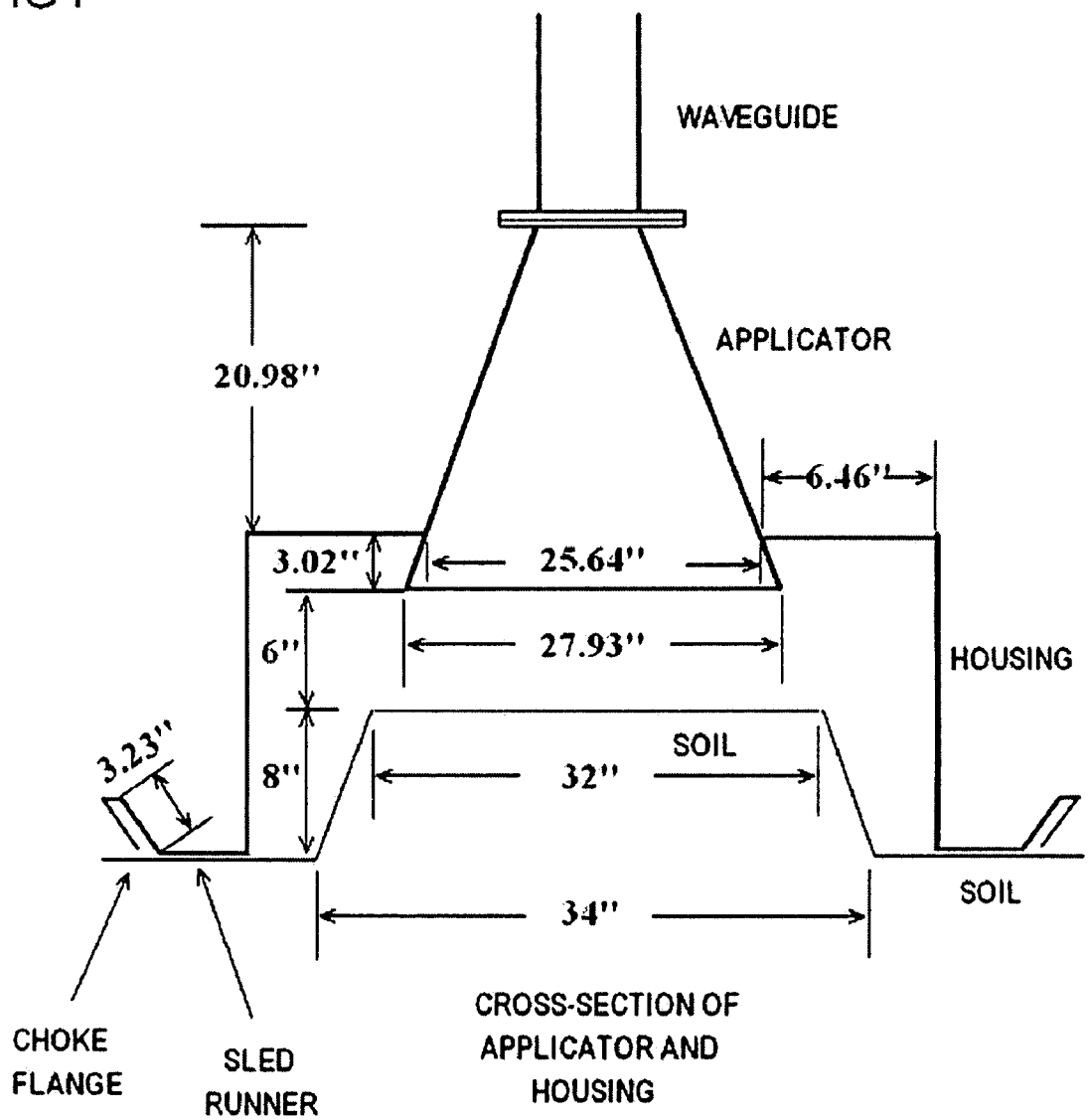
FIG. 4 is a planar cross-sectional view of an application of the present invention with an operating frequency of 915 MHz. All dimensions shown are only exemplary.
Figure 5:
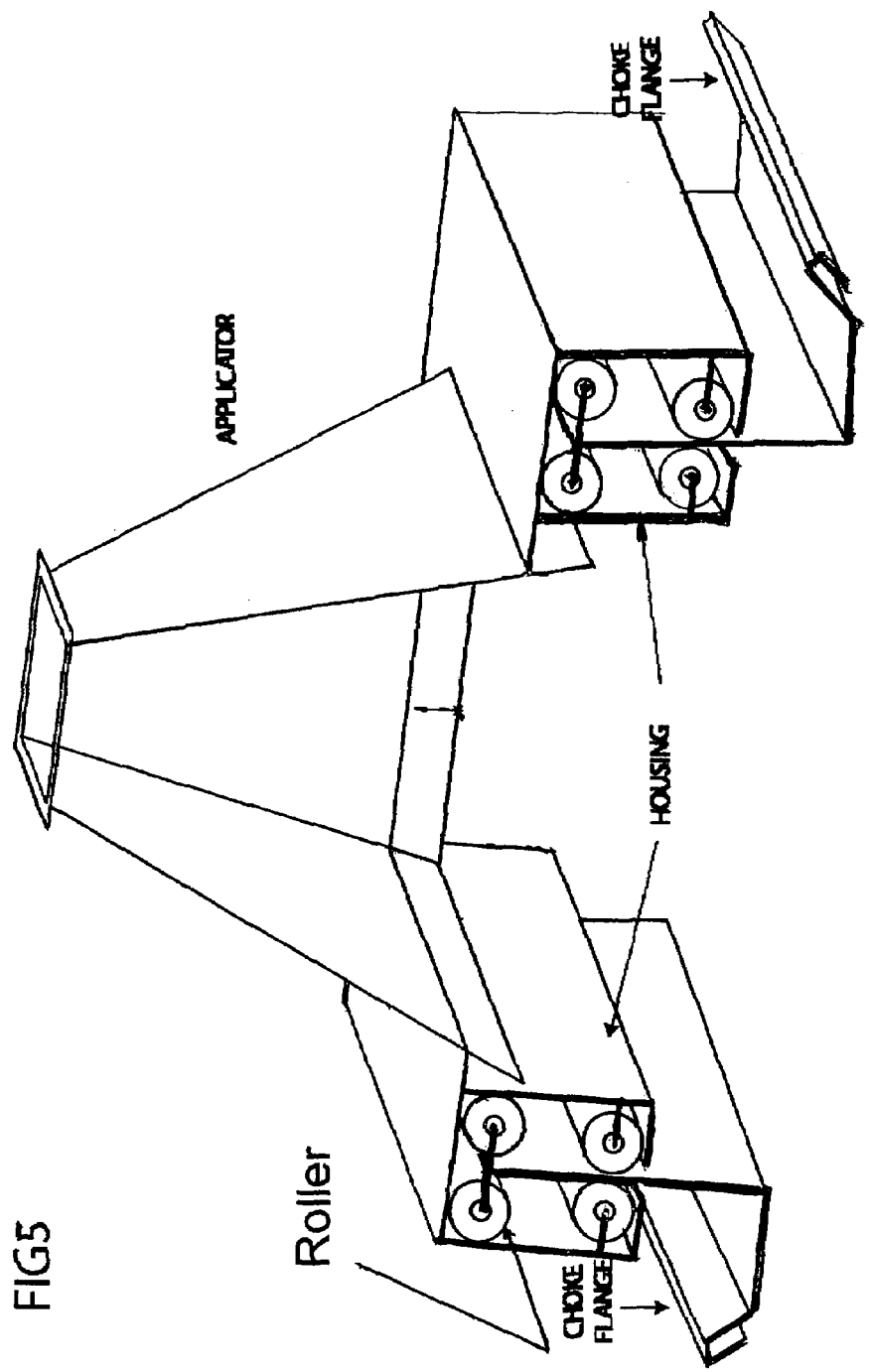
FIG. 5 is an alternate three dimensional view of a cross section of the present invention.

FIG. 1 shows one embodiment of the invention as it would be used on crop soil that has been prepared for planting. The raised and flat-topped rows are approximately 8 inches tall and 34 inches wide at the base. The dimensions and arrangement of individual parts of the applicator are constructed to conform to the crop row dimensions, and furthermore to distribute the microwave energy over the width of the row while preventing energy leakage into the outside environment. The microwave generator and the waveguides or transmission lines that connect it to the applicator are commercially available, and are well known to those skilled in the art. It will be appreciated by those skilled in the art that a wide variety of microwave generators, waveguides and/or transmission lines may be used in conjunction with the present invention.

It is preferable to connect the output port of the portable microwave generator to the input port of the applicator via a waveguide section. However, the input port of the applicator may be connected directly to the output port of the portable microwave generator.

It is important to note that it is preferable to optimize the shape of the waveguide that may guide the microwave transmission into infested soil. The shape of the waveguide, with respect to the microwave power and frequency, should be such that the raypaths of the microwave energy would enter the ground at a angle perpendicular to the soil. This minimizes reflections from the ground causing a maximization of electromagnetic energy into the soil and thus into the pests and insects located within the soil.

An embodiment of the invention includes metal slats or "sled runners." These metal slats are made of a microwave reflective material, such as any metal. The metal slats stay in contact with the soil on each side of the crop row to prevent the loss of energy into the environment, thus maintaining the efficiency and safety of the invention. These metal slats of the present invention cover different applicators and leakage suppression structures, sled runners and wheels, parabolic reflectors, corner reflectors, horns with no cowl. The metal slats may comprise rollers at the end of the metal slats which make contact with the soil. This allows the metal slat to stay as close to the soil, instead of "bouncing," while the vehicle is in motion, especially when traveling over bumps, crop rows or any other section of the land where there may be substantial topography.

In any of the Figures where pairs of metal rollers are shown, the axes of the lower pair of rollers are attached to the central metal sheet (of the three that are parallel and vertical), and the axes of the upper pair of rollers are attached to the nearest of the outer metal sheets (of the three that are parallel and vertical). The central metal sheet is connected to the cowl or housing that is attached to the applicator or horn antenna. This arrangement allows up and down movement of the lower part of the cowl or housing that is attached to the metal sled runners. Thus, if the sled runners encounter an obstruction, for example, a rock or a piece of wood, the bottom part of the cowl or housing will move upward by a maximum of approximately 6 inches. The Figures show the lower part of the cowl or housing in the maximum downward position. In the maximum upward position, all pairs of rollers would be touching. The pairs of rollers may be mounted at any vertical position along the cowl or housing, including the top or the bottom. The same arrangement of pairs of rollers could also be mounted on the vertical rectangular waveguide that applies microwave energy to the horn antenna.

In addition to metal slats or sled runners, leakage suppressors or "choke flanges" may be placed at the end of the applicator or metal slats in order to suppress microwave leakage and/or radiation. The leakage suppressors or choke flanges are generally a quarter-wavelength in length.

The power of microwave signals propagating through soil is attenuated with respect to distance (z) into the soil as, $$P(z) = P_0 e^{-2z/\delta} \quad (1)$$

where $$\delta = \frac{\sqrt{\varepsilon_s}}{(60\pi\sigma_s)} \quad (2)$$

is the so-called depth of penetration, $\varepsilon_s$ is the relative dielectric constant of the soil (usually ranging from 4 to 7), $\sigma_s$ is the conductivity of the soil (usually less than 0.025 S/m) and $P_0$ is the power in watts per square meter entering the soil surface at z=0. Equation (2) is valid for determining $\delta$ if $\sigma_s \leq 0.0056 f_G \varepsilon_s$, where $f_G$ is the microwave frequency in GHz. Thus, for $\varepsilon_s=5$ and $f_G=0.915$, (2) is valid for all $\sigma_s \leq 0.025$ S/m, the usual range for soil conductivity, and for these parameter values $\delta \geq 0.475$ m=1.56 ft. Designating the soil as damp ($\sigma_s=0.025$ S/m), normal ($\sigma_s=0.015$ S/m) and dry ($\sigma_s=0.005$ S/m), the corresponding depths of penetration are, respectively: 1.56 ft, 2.60 ft and 7.80 ft.

When heating insects at a particular depth within the soil, the microwave energy must pass through the soil to reach the insects at that depth. The equation used to make this calculation assumes that the target insect is small compared with wavelength. For example, at 0.915 GHz (915 MHz) the wavelength in soil is approximately 0.15 m=150 mm, and the target insects are typically less than few millimeters in diameter.

Thus, the power absorbed in watts per cubic meter by an insect at any depth z includes equation (1) and is expressed as [1]:

$$P_a(z) = \frac{9\sigma_i(120\pi/\sqrt{\varepsilon_s})P_0 e^{-2z/\delta}}{\left(\frac{\varepsilon_i}{\varepsilon_s}+2\right)^2 + \left(\frac{18\sigma_i}{f_G\varepsilon_s}\right)^2} \quad (3)$$

For example, if $P_0=100$ kW/m², $f_G=0.915$, $\sigma_i=3$ S/m and $\varepsilon_i=49$, then:

$$P_a(z) = 1.599 \times 10^6 e^{-2z/\delta} \text{W/m}^3 = 1.599 e^{-2z/\delta} \text{W/cm}^3 \quad (4)$$

It may be assumed that the moisture within the insect is heated by the absorption of microwave energy. Using the fact that 1 calorie of energy will increase the temperature of 1 gram of water by 1° C., the initial rate of temperature increase in the insect is determined by:

$$P_a = K\rho c dT/dt = 4.186 \text{ joules/cal} \times 1 \text{ gm/cc} \times 1 \text{ cal}/(\text{gm}° \text{C.})(° \text{C./sec}) = \text{W/cm}^3 \quad (5)$$

Thus, $$dT/dt = (1.599/4.186)e^{-2z/\delta_0} \text{ C./sec} = 0.382 e^{-2z/\delta_0} \text{ C./sec} \quad (6)$$

For dry soil conditions, the initial rate of temperature increase within an insect at various depths within the soil is determined from (6) as: z=0, dT/dt=0.382° C./sec=60.38° C./min; z=0.25 δ=1.95 ft, dT/dt=0.232° C./sec=13.92° C./min; z=0.5 δ=3.90 ft, dT/dt=0.141° C./sec=8.46° C./min and z=δ=7.8 ft, dT/dt=0.052° C./sec=3.12° C./min.

The above applications of the instant invention have been used at 915 MHz. This invention is not limited to this frequency. This invention, including dimensions, microwave source and other relevant parameters, may be modified to a frequency lower than 915 Mhz in order to obtain a greater depth of penetration into the soil. Conversely, the operational microwave frequency may be increased, e.g. 2.45 GHz, in order to increase the concentration of microwave energy into the uppermost layer of the soil.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A microwave system comprising:
   a portable microwave generator capable of outputting microwave energy and comprising a first output port, said portable microwave generator is mounted on a vehicle;
   an applicator mounted to the vehicle and comprising applicator housing, an input port and at least one microwave leakage suppressor, said at least one microwave leakage suppressor comprises metal sled runners that make contact with the land;
   a roller system which makes direct and continuous contact with the metal sled runners and the applicator housing while the vehicle is in motion so that said metal sled runners are capable of free movement within said roller system in a direction that is perpendicular to the ground; and a means for transporting microwave energy from said first output port to said input port;

wherein said applicator housing is adapted and configured to conform to the topography of a soil crop row;

wherein said portable microwave generator is arranged and configured to said applicator to transfer outputted microwave energy from said portable microwave generator into a section of land; and wherein each of said metal sled runners comprises:

a first portion extending substantially perpendicularly to the ground and having a distal end and a proximate end, said proximate end contacting said applicator;

a second portion extending from said distal end of said first portion along a surface of a section of the ground so that said second portion directly makes contact with the ground;

wherein said first and second portions are directly connected to each other so as to be in direct electrical communication with each other; and wherein said first and second portions are planar elements and said second portion having a flat planar surface that makes substantially flush contact with the ground.

2. The microwave system of claim 1, wherein said roller system comprises at least two rollers, a metallic means that connects said at least two rollers to the applicator housing, wherein the roller system allows the metal sled runners to contract and expand relative to the applicator housing while the vehicle is in motion in order to compensate for changes in soil topography.

3. The microwave system of claim 1, wherein said applicator further comprises a waveguide.

4. The microwave system of claim 3 wherein the shape of said waveguide is such that the microwave energy enters the soil at an angle approximately perpendicular to the soil.

5. The microwave system of claim 1, wherein said portable microwave generator operates at a frequency of 915 Megahertz.

6. The microwave system of claim 1, wherein said outputted microwave energy is sufficient to kill insects living in said section of land.

7. The microwave system of claim 1, wherein said applicator housing comprises a sidewall having an edge proximate to the ground, said edge adapted to be arranged transversely to said soil crop row and said sidewall edge having a non-linear shape so as to receive said soil crop row.

8. The microwave system of claim 7 wherein said edge comprises at least an edge portion having an inverted "U" shape for receiving said soil crop row.

9. The microwave system of claim 1, wherein said first and second portions are connected so as to form an "L"-shaped member and wherein said second portion of said metal sled runner extends from said distal end of said first portion of said metal sled runner in a direction away from an internal space defined by said applicator housing and ground located directly underneath said applicator housing.

10. The microwave system of claim 1, wherein said first portion comprises a planar sheet of metal extending perpendicular to the ground and extending lengthwise along one side of said applicator housing, and said second portion comprises another planar sheet of metal connected perpendicularly to said first portion and extending substantially parallel said section of ground in a direction away from said input port, wherein said second portion is the only portion of said applicator that makes direct contact with the ground.

11. A method of directing microwave energy into soil comprising:

activating a portable microwave generator that is arranged and configured to an applicator and mounted on a vehicle, wherein said applicator comprises at least one metal sled runner which makes contact with the soil; and operating said vehicle so as to transfer outputted microwave energy from said portable microwave generator into the soil;

wherein said microwave system comprises a roller system which makes direct and continuous contact with the metal sled runners and the applicator housing while the vehicle is in motion so that said metal sled runners are capable of free movement within said roller system in a direction that is perpendicular to the ground; and wherein each of said metal sled runners comprises:

a first portion extending substantially perpendicularly to the ground and having a distal end and a proximate end, said proximate end contacting said applicator;

a second portion extending from said distal end of said first portion along the ground and extending in a direction away from an internal space of said applicator;

wherein the first and second portions are connected to each other so as to be in direct electrical communication with each other; and wherein the first and second portions are planar elements and said second portion having a flat planar surface that makes substantially flush contact with the ground.

12. The method of claim 11, wherein said vehicle is continuously operated to direct microwave energy over a continuous strip of soil.

13. The method of claim 11, wherein said outputted microwave energy is sufficient to kill insects living in said soil.

14. The method of claim 11, wherein said portable microwave generator operates at a frequency of 915 Megahertz.

* * * * *